United States Patent
Kunkel et al.

[11] Patent Number: 5,871,354
[45] Date of Patent: Feb. 16, 1999

[54] APPLICATOR FOR DENTAL FILLING MATERIALS

[75] Inventors: Peter Kunkel, Triesen; Jürgen Mertins, Gams, both of Germany

[73] Assignee: Ivoclar AG, Schaan, Liechtenstein

[21] Appl. No.: 851,365

[22] Filed: May 5, 1997

[30] Foreign Application Priority Data

May 8, 1996 [DE] Germany ............................ 19618544.0

[51] Int. Cl.$^6$ ...................................................... A61C 5/04
[52] U.S. Cl. ................................................. 433/89; 433/90
[58] Field of Search ........................ 433/89, 90; 604/135; 222/391, 386, 326

[56] References Cited

U.S. PATENT DOCUMENTS

| | | | |
|---|---|---|---|
| 4,090,639 | 5/1978 | Campbell et al. | 222/391 |
| 4,330,070 | 5/1982 | Doubleday | 222/391 |
| 4,382,789 | 5/1983 | COlombo et al. | 433/89 |
| 4,681,524 | 7/1987 | Ikeda et al. | 222/326 |
| 4,840,294 | 6/1989 | Ernst | 222/391 |
| 5,192,008 | 3/1993 | Hwan | 222/391 |

FOREIGN PATENT DOCUMENTS 36 07 384  9/1986  Germany .

*Primary Examiner*—John J. Wilson
*Attorney, Agent, or Firm*—John C. Thompson; Alan S. Korman

[57] ABSTRACT

An applicator for highly viscous materials such as dental filling materials has a housing and a first and second jamming element positioned spaced from one another in a longitudinal direction in the housing. A coupling rod is connected to the second jamming element. A piston rod is supported in the housing. An actuating element is positioned at the housing and connected to the piston rod for moving the piston rod in a forward direction from an inactive position into a working position, and in a rearward direction from the working position into the inactive position. The first jamming element is jammed, when the actuating element actuates the piston rod in the forward direction, and is moved with the piston rod in the forward direction. The second jamming element is jammed by a spring force in the rearward direction so as to rest at the housing, when the actuating element actuates the piston rod in the forward direction. The actuating element, when moving the piston rod in the rearward direction, acts on the coupling rod for releasing the second jamming element.

21 Claims, 4 Drawing Sheets

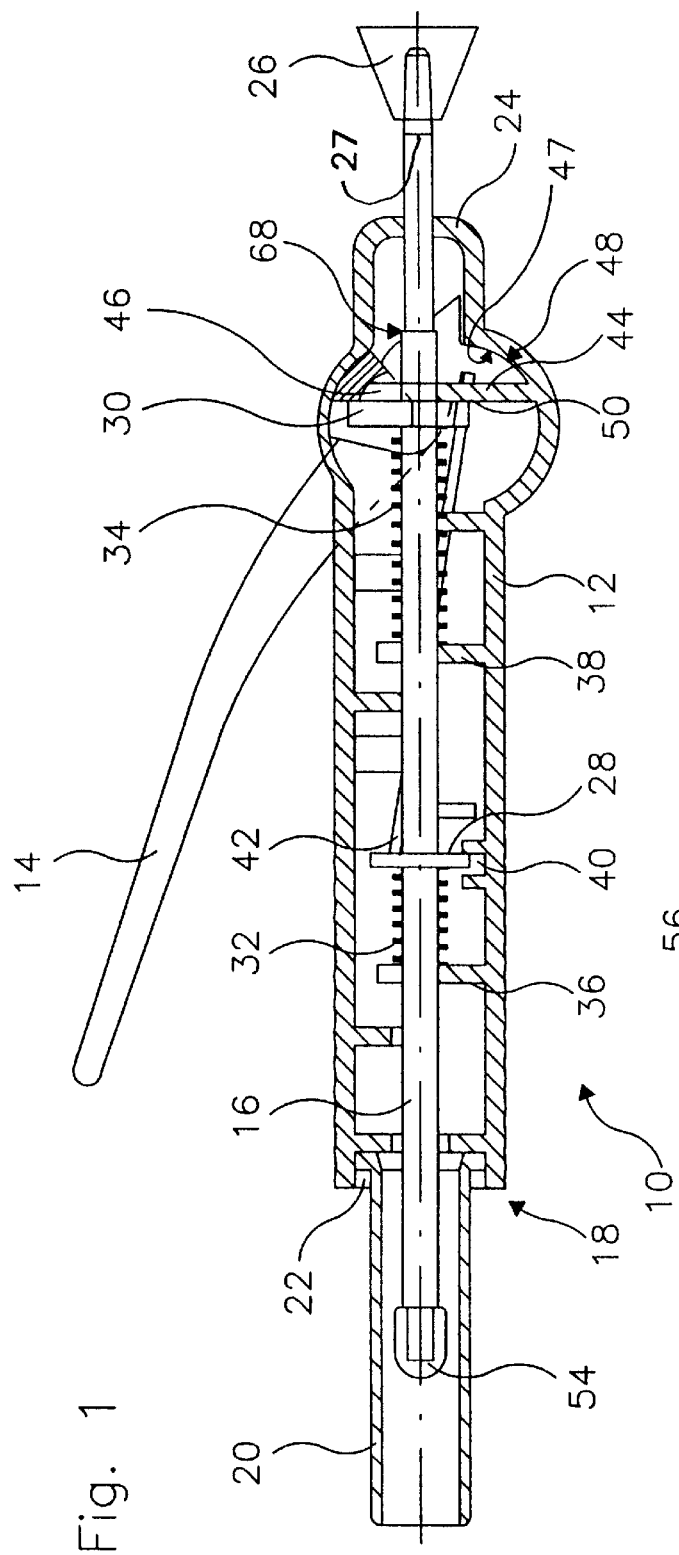
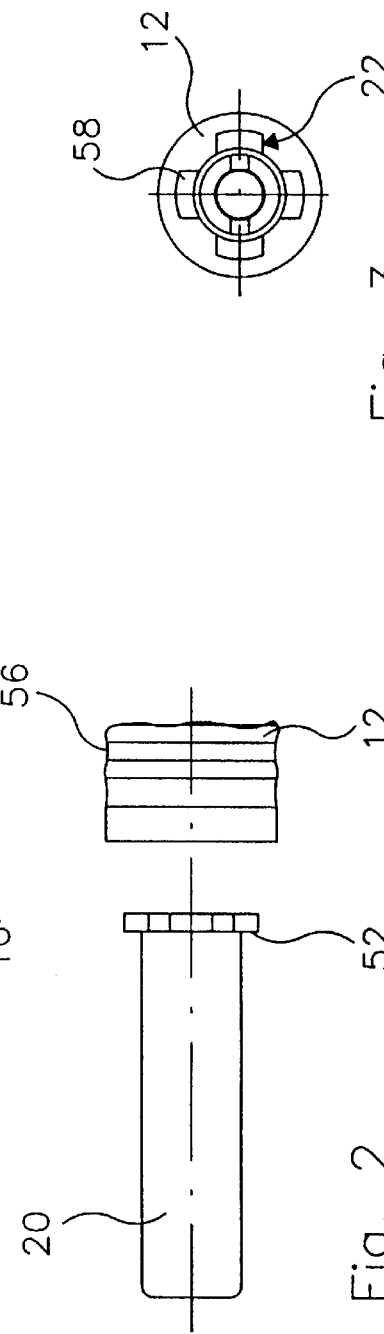

APPLICATOR FOR DENTAL FILLING MATERIALS

BACKGROUND OF THE INVENTION

The present invention relates to an applicator, especially for highly viscous materials, comprising a housing and a piston rod supported in the housing which upon actuation by an actuating element is displaced from an inactive position into a working position, i.e., upon movement in the working direction, is movable by passing two serially arranged jamming elements in the forward direction, whereby an actuator jamming element upon actuating the actuator element is jammed and displaced forwardly together with the piston rod and a locking jamming element is jammed by spring-loading into the rearward direction and supported at the housing.

Such an applicator for highly viscous materials, especially for dental filling materials, is, for example, known from German Offenlegungsschrift 36 07 384. This applicator comprises a pistol grip with a pressing element that dispenses the dental filling material via a drive mechanism with each actuation. When the cartridge with the dental filling material is empty, the piston rod can be released by a release rod and returned so that a new full cartridge can be inserted.

Dental filling materials, in general, must be exactly metered so that it is desirable that the amount of material dispensed upon actuation of the pressing element is constant. Especially, it is desired that the actuation will prevent further flowing of the pastelike or the highly viscous material, especially since this is frequently going hand in hand with contamination. In the solution known from German Offenlegungsschrift 36 07 384, for avoiding further unwanted oozing of the dental filling material from the dispensing opening, it is provided that upon actuation of the pressing element or actuating element, subsequently to the dispensing process, a pressure relief of the piston rod with a special relief lever is performed which is a unitary part of the actuating lever and acts on a locking jamming element.

It is disadvantageous in this apparatus that pressure relief can only be performed when the pressing element has completed its entire stroke. On the other hand, an operator, after completed pressing of the desired amount, has the tendency not to apply any further force in order to complete the stroke of the pressing element, especially since the desired dispensing effect has already been achieved. Accordingly, it is not ensured that unwanted dispensing can be prevented with this apparatus.

It is therefore an object of the present invention to provide an applicator of the aforementioned kind which reliably prevents unwanted dissension (oozing) of the material to be applied from the dispensing opening.

SUMMARY OF THE INVENTION

The applicator for highly viscous materials according to the present invention is primarily characterized by:

A housing;

A first and a second jamming element positioned spaced from one another in a longitudinal direction in the housing;

A coupling rod connected to the second jamming element;

A piston rod supported in the housing;

An actuating element positioned in the housing and connected to the piston rod for moving the piston rod in a forward direction from an inactive position into a working position, whereby the actuating element is moved from a rest position into an operative position and in a rearward direction from the working position into the inactive position;

Wherein the first jamming element is jammed, when the actuating element actuates the piston rod in the forward direction, and is moved with a piston rod in the forward direction;

Wherein the second jamming element is jammed by a spring force in the rearward direction so as to rest at said housing, when the actuating element actuates the piston rod in the forward direction; and Wherein the actuating element, when moving the piston rod in the rearward direction, acts on the coupling rod for releasing the second jamming element.

Preferably, the coupling rod in the rest position of the actuating element acts on the second jamming element, and the piston rod in its inactive position is freely movable.

The actuating element is movable past in the rest position in the rearward direction into a release position such that the piston rod is freely movable.

The actuating element is a handle extending in the rest position at an acute angle to the piston rod. It is displaced toward the housing in order to reach the operative position and is moved away from the housing to return into the rest position.

The acute angle is approximately 26°.

When the actuating element is moved from the rest position into the operative position, the first jamming element acts on as a one-arm lever onto the piston rod and the actuating element is supported at the housing.

The actuating element is a lever that is spring-loaded into the rest position, the lever having a free end pointing substantially in the forward direction.

The actuating element comprises a follower acting onto the first jamming element such that, when the actuating element is moved from the rest position into the operative position, the first jamming element is pressed onto the piston rod in the forward direction.

The coupling rod extends between the second jamming element and the actuating element and is supported at a support location at the actuating element, wherein the support location is spaced from the follower.

The coupling rod extends at a slant to the piston rod and projects past the actuating element.

The coupling rod preferably has opposite ends and a joint at each one of the opposite ends.

The coupling rod is a push rod and has a length such that, upon return of the actuating element from the operative position into the rest position, the second jamming element is released.

The second jamming element, viewed in the forward direction, is arranged in front of the actuating element.

The housing has an abutment for the first jamming element arranged such that in the rest position of the actuating element the second jamming element is positioned, without being jammed, on the piston rod.

The coupling rod is a release rod for ensuring jamming of the second jamming element during a last portion of a return travel of the actuating element into the rest position and the piston rod, during the return travel of the actuating element, is easily movable in the rearward direction.

The applicator further comprises a connector for attaching thereto a cartridge containing a highly viscous material in the form of a dental filling material.

Preferably, the piston rod has a rearward end projecting from the housing and having a marking for indicating an end position for a travel stroke of the piston rod in the forward direction corresponding to a complete emptying of a cartridge attached to a forward end of the housing, the cartridge containing the highly viscous material.

The housing may comprise a connector for an adaptor, guiding a piston spring-loaded in the rearward direction and comprising a snap-on receiving member for a cartridge containing a light-curing dental filling material.

Preferably, the coupling rod extends at an acute angle to the piston rod.

The piston rod has a step for disengaging, at the end of the travel stroke of the piston rod into the working position, the first jamming element from the piston.

The piston rod comprises a micro toothing at least in the area of the first jamming element.

It is especially advantageous with the inventive applicator or the inventive dispensing device that an automatic return into a relief position for the material to be dispensed is provided, independent of whether the actuating element is completely or only partly moved along its actuating travel stroke. In this context it is especially advantageous that the release with the inventive coupling rod takes place during release of the actuating element.

Due to the lever effect of the actuating element or lever, a force transmission of, for example, 5:1 is generated so that the dispensing force is, for example, five times greater than the actuating force of the actuating lever. The dispensing force is received by the piston rod, the jamming elements, and the housing which each have a certain elasticity so that a minimal elastic return travel upon release of the actuating force results. This elastic return travel is inventively also taken into consideration so that the cartridge inserted into the applicator or a cartridge attached via an adaptor remains tension-(stress)-free when the actuating element is in the rest position. Inventively, it is thus provided that even the required elasticity of the working elements is uncritical during actuation of the device.

According to a first embodiment, the piston rod in the rest position of the actuating element is freely movable. Accordingly, it can be easily pulled to the rear for loading a new cartridge. In this embodiment, the length of the coupling rod is such that in the rest position of the actuating element it is under pressure and releases the locking jamming element. Only upon release of the actuating element after travel into the operative position, the locking jamming element engages, but only over a portion of the travel distance of the actuating element in the rearward direction, so that during the remaining portion of the travel distance of the actuating element the locking jamming element is disengaged and due to the friction between the locking jamming element and the actuating element a small return movement of the piston rod, i.e., a movement in the rearward direction, occurs.

In a second embodiment of the invention, it is in contrast thereto suggested that the length of the coupling rod is dimensioned such that the locking jamming element in the rest position of the actuating element still engages, i.e., it jams the piston rod. In this embodiment a reliable pressure relief and optionally also a small movement of the piston rod in the rearward direction can also be realized with a suitable adjustment. For a complete movement of the piston rod in the rearward direction, for the purpose of exchanging the cartridges, it is suggested in this embodiment that the actuating element be movable past its rest position into a release position in which it acts on the piston rod so that the piston rod moves the locking jamming element counter to its spring loading into a release position in which the piston rod is freely moveable.

According to a further preferred embodiment a control device is provided with which the distance, defined by the coupling rod, between a surface of the actuating element and the locking jamming element is adjustable. The control device can be embodied in any suitable manner, for example, as a knurled nut, positioned on the coupling rod and accessible from the exterior, or a slidable bearing location of the jamming locking element at the housing. It is also possible, with a further embodiment of the inventive applicator, depending on the position of the control device, to provide a counter movement of the piston rod in the rearward direction shortly before reaching the rest position of the actuating element or to ensure a simple pressure relief of the cartridge containing the highly viscous material.

It is preferred that the inventive applicator empties the cartridge containing the highly viscous material by a plurality of strokes. When a cartridge containing light-curing material is used with interposition of an adaptor, it may be, for example, provided that the piston rod performs approximately 3 to 20 strokes, preferably 5 to 12 strokes, and especially 8 to 9 strokes, for emptying the cartridge so that the stroke of the piston rod, for each complete travel stroke of the actuating element and an assumed filling length of the cartridge of 1.5 cm, is 0.8 to 5 mm and especially approximately 1.9 mm, It is understood that the number of possible strokes for a complete emptying of the piston rod from one end to the other may be adjusted in wide ranges according to the respective requirements. For examples, the piston rod can also have a substantially increased travel stroke of approximately 10 cm when a correspondingly large cartridge has to be serviced.

Also, the transmission ratio of the lever acting as an actuating element can be adapted within wide ranges to the respective requirements. For a stroke of 4 mm, it may be, for example, provided that the free end of the actuating lever is moved by approximately 4 cm so that accordingly the travel stroke transmission ratio, respectively, force transmission ratio is 1:10, respectively, 10:1.

The inventive solution allows, despite its good transmission ratio, a relatively compact and especially ergonomic design. The slanted rest position of the actuating lever which is pointed in the forward direction of the piston rod and is pivotable relative to the housing in order to produce a working stroke, i.e., a movement of the piston rod in the forward direction, allows, for example, that the forward end of the housing or optionally the cartridge sleeve or the adaptor can be held with two or three fingers, while the thumb points in the rearward direction of the piston rod and supports the housing at a suitable location so that, for example, the index finger or middle finger can be used for actuating the actuating element as desired. This grip position provides for a steady holding without causing movement of the dispensing end when the actuating lever is operated. Surprisingly, the actuating action in this grip position is even more steady and constant than the use of a pistol grip of known applicator devices, even though the inventive applicator is of a substantially smaller design and has a substantially smaller weight so that working without fatigue is possible.

Instead of the afore-described grip position, it is also possible to grip the housing with four fingers and to place the thumb onto the tip or the free end of the actuating lever. In this position a relatively steady operation of the inventive applicator is also possible, for positions in which the dispensing opening of the applicator points in the upward as well as in the downward direction relative to the closed hand.

It is inventively especially advantageous when the cartridge contained in a sleeve or the adaptor for receiving a cartridge are connected with a snap-on connection, for example, in the form of a bayonet closure, to the housing whereby the housing is extended in this manner. Then the entire applicator has substantially rod shape and the remaining reserve of the cartridge can be easily read with the aid of corresponding markings that are positioned at the rearward end of the piston rod which projects from the rear of the housing.

The adaptor can be provided, if needed, with a rather soft return spring which acts in the direction of pressure relief of the cartridge. Upon actuation of the actuating element into the release position, this causes the piston rod to be automatically returned into its inactive position so that a new cartridge can be attached. The force of the return spring is preferably so minimal that it is not sufficient to return the piston rod into its inactive position when the actuating element is in its rest position, but only provides a pressure relief of the cartridge after each stroke.

BRIEF DESCRIPTION OF THE DRAWINGS

The object and advantages of the present invention will appear more clearly from the following specification in conjunction with the accompanying drawings, in which:

FIG. 1 shows a schematic sectional view of one embodiment of the inventive applicator;

FIG. 2 shows a front view of the applicator with separate cartridge sleeve;

FIG. 3 is a front view of the forward end of the applicator whereby the cartridge sleeve has been removed;

DESCRIPTION OF PREFERRED EMBODIMENTS

Figure 4:
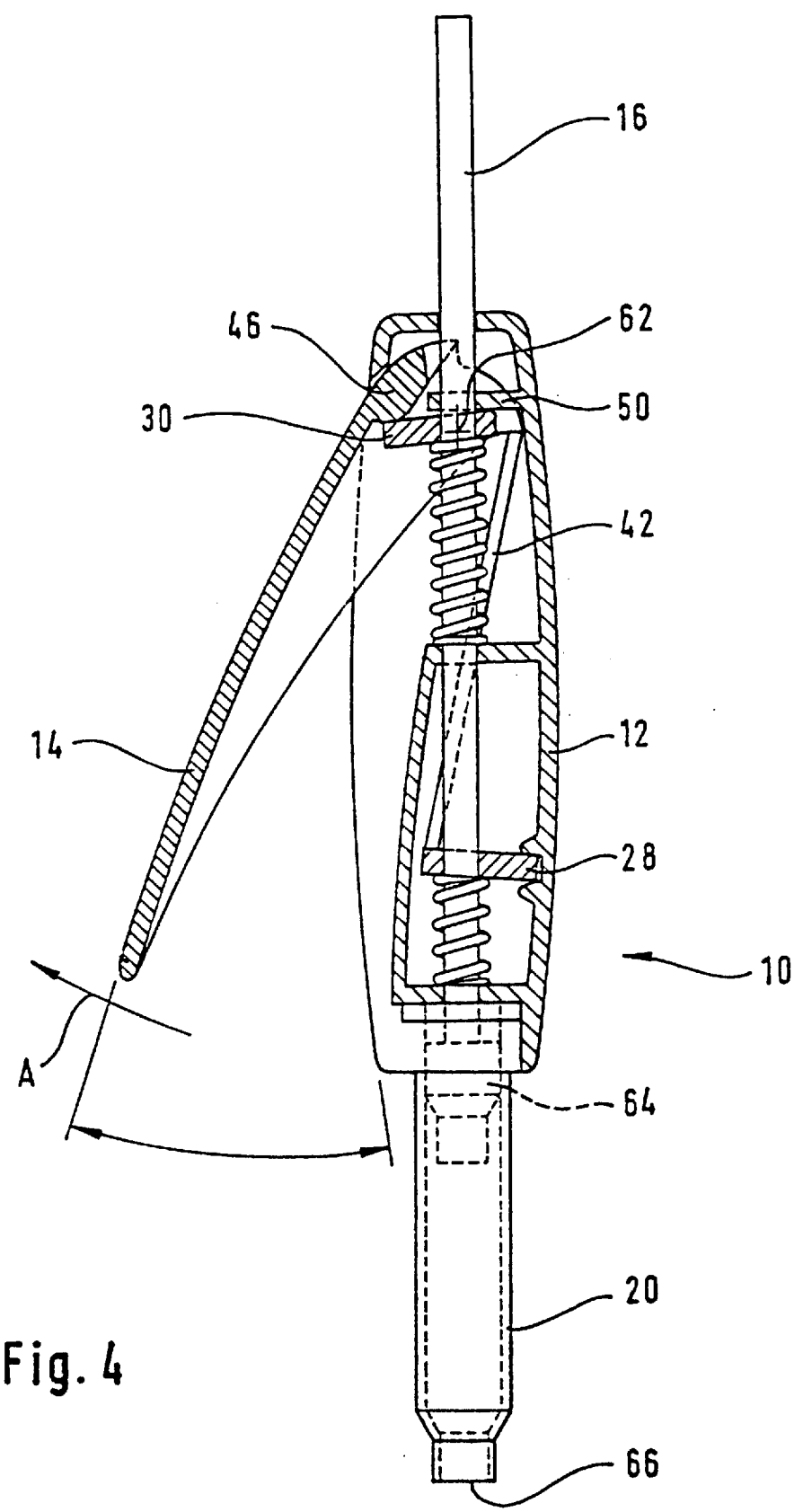
FIG. 4 is a schematic view of a further embodiment of the inventive applicator.

The present invention will now be described in detail with the aid of several specific embodiment utilizing FIGS. 1 through 7.

A first embodiment of the applicator is represented in FIG. 1. The applicator 10 comprises a housing 12 that includes an actuating lever 14 functioning as an actuating element which is pivotably guided and supported at the housing 12. The housing 12 furthermore includes a displacebly supported piston rod 16. At its forward end 18 it has a cartridge sleeve 20 for a non-represented cartridge containing the dental filling material. The cartridge sleeve 20 is detachably connectable via the adaptor connector 22, especially in the form of a bayonet closure, to the housing 12.

The piston rod 16 penetrates the housing at its rearward end 24 and ends in a grip 26. The grip 26 allows the manual return of the piston rod 16 into its inactive position in which the piston rod 16 is in the extreme right position as shown in FIG. 1.

The inventive applicator 10 comprises a locking jamming element 28 (second jamming element) and an actuator jamming element 30 (first jamming element). Both jamming elements extend substantially annularly about the piston rod 16. In order to ensure jamming by tilting, they have an inner diameter which is slightly greater than the outer diameter of the piston rod 16. The inner surface of the jamming elements 28 and 30 is flat, in a manner known per se, and ends relatively sharp-edged in order to ensure the desired jamming action upon tilting.

Both jamming elements 28, 30 are spring-loaded by pressure springs 32, 34 in the rearward direction of the piston rod, i.e., in the direction toward the grip 26. The pressure springs 32, 34 are supported at their ends remote from the jamming elements 28, 30 at a respective support projection 36, 38 of the housing 12 and extend coaxially about the piston rod 16.

The second jamming element 28 is furthermore supported at one side in a receiving unit 40 of the housing 12. Due to the action of the pressure spring 32, the second jamming element 28 is tilted and thus locks movement of the piston rod 16 in the rearward direction. On the other hand, a movement of the piston rod under frictional load in the forward direction is possible because then the piston rod 16 entrains the second jamming element 28, against the force of the pressure spring 32, by a small distance and reduces the jamming force.

At the side opposite the receiving unit 40, a coupling rod 42 is connected to the second jamming element 28 and acts also counter to the force of the pressure spring 32. In the shown embodiment according to FIG. 1, the coupling rod 42 is supported with its other end at the actuator jamming element 30. The coupling rod 42 extends at a slant to the piston rod 16 whereby it is understood that instead of the represented embodiment also other force-transmitting devices, for example, a sleeve, a longitudinal element etc. can be used for transmitting the pressure force onto the second jamming element 28.

In the represented embodiment the length of the coupling rod 42 is selected such that, in the rest position of the actuating element 14, the coupling rod 42 presses onto the second jamming element 28 such that the piston rod 16 is released. The piston rod 16 is thus freely movable.

The first jamming element 30 extends in a similar manner as the second jamming element 28 about the piston rod 16. Accordingly, the actuator jamming element 30 is able to secure itself upon tilting to the piston rod 16 at least in one direction. While the second jamming element 28 is supported in a receiving unit 40 in the forward as well as in the rearward direction, the first jamming element 30 rests only with one side on an abutment 44 of the housing 12. The abutment 44 supports the jamming element 30 in the rearward direction.

The actuating element 14 comprises a follower 46 which is fixedly connected thereto and which is designed for resting at the actuating jamming element 30. For this purpose, the actuating jamming element 30 has an abutment surface in the rearward direction. Upon actuation of the actuating element 14 in a counter clockwise direction, in the representation of FIG. 1, the follower 46 is entrained in the forward direction and acts thus one-sidedly onto the first jamming element 30. Since the pressure spring 34 acts in the counter direction, the first jamming element 30 is tilted and jams and is thus able to move with the piston rod 16 in the forward direction.

The actuating element 14 is pivotably supported at the housing 12. For this purpose, an axle of the actuating element 14 can extend transverse through the housing. Instead, it is also possible; to provide correspondingly shaped guide surfaces 47,48 between the housing 12 and the actuating element 14 on which the actuating element 14 can glide so that the desired pivoting action is ensured.

In the represented embodiment according to FIG. 1, the pivot axis of the actuating element in the form of a pivot lever 14 extends in the area of the coupling rod 42 and the actuator jamming element 30. The actuating element 14 comprises furthermore a support location 50 for the coupling rod 42 at a side of the lever 14 opposite the follower 46 relative to the pivot axis. Upon movement of the follower 46 in the forward direction, the support location 50 thus moves in the rearward direction so that the coupling rod 42 is also moved in the rearward direction and the jamming element 28 jams under the force of the pressure spring 32.

The actuation of the actuating device 14 from the rest position, represented in FIG. 1 into the operative position, into which the lever 14 has been pivoted counter clockwise so as to rest at the housing 12 or to at least extend in its vicinity, has the effect that first the first jamming element 30 is tilted by the follower 46 and initiates the movement of the piston rod 16 is moved in the forward direction. At the same time, the coupling rod 42 is relieved so that the second jamming element 28 begins to tilt. As soon as the movement in the counter clockwise direction begins, the jamming element 28 is completely relieved so that the piston rod 16 can be moved in the forward direction, but not in the rearward direction.

Upon reaching the operative position, the travel stroke of the actuating element 14 in the working direction (forward direction) is complete. In this position, the movement of the actuating element 14 in the counter direction can be started. The pressure spring 34, which due to the joint displacement of the actuator jamming element 30 and the piston rod 16 has been compressed, supports the movement of the actuating element 14 in the counter direction. The coupling rod 42 initially does not act on the jamming element 28 so that the piston rod 16 is locked in the rearward direction. Upon release of the actuating element 14, the first jamming element 30 thus glides in the rearward direction along the piston rod 16. This takes place until a position of the actuating element or lever 14 has been reached in which the support location 50 activates the coupling rod 42, especially by pressure loading. Accordingly, the jamming element 28 is released, and the piston rod 16 is thus also released. Due to the friction between the still tilted jamming element 30 and the piston rod 16, the piston rod 16 is now moved in the rearward direction until the rest position of the actuating element 14 shown in FIG. 1 is reached.

It is understood that with a suitable selection of the length of the of the coupling rod 42 relative to the distance between the jamming element 28 and the support location 50, the position of the actuating element 14 at which the rearward movement of the piston rod 16 will begin, is adjustable, The rearward movement serves for the specific pressure relief of the material to be dispensed in order to thus reliably prevent any additional dispensing or oozing of material from the outlet opening.

The stroke of the inventive applicator 10 is defined by the forward movement of the piston rod 16 minus the small rearward movement for avoiding the unwanted dispensing (oozing). The piston rod has a marking 27 for indicating an end position for a travel stroke of the piston rod in the forward direction corresponding to a complete emptying of a cartridge attached to the forward end of the housing.

FIG. 2 show s the cartridge sleeve 20 in a state before it is attached to the housing 12, The cartridge sleeve 20 is provided at the end facing the housing 12 with four adaptor projections 50. The cartridge contains the highly viscous material, especially a dental filling material, that is to be dispensed by the inventive applicator 10. For this purpose, the piston rod 16 with its forward end provided with a plunger 54 acts onto a piston of the cartridge that thus dispenses the dental filling material, especially a light-curing dental filling material.

As can be seen in particular in FIG. 2, the housing 12 at its outer circumference is provided with a fluting (micro toothing) 56 at its forward end in order to improve manipulation thereof.

As can be seen in FIG. 3, the adaptor connector 22 is in the form of a bayonet closure. Adaptor projections 52 extend uniformly distributed about the periphery of the cartridge sleeve 20 and are suitable to engage correspondingly shaped recesses 58 at the forward end of the housing 12. Upon rotation of the cartridge sleeve about 45°, a locking of the adaptor projections 52 at the adaptor connector 22 is achieved so that the cartridge sleeve 20 is securely and bending-resistantly connected to the housing 12.

Another embodiment that slightly deviates from the embodiment of FIG. 1 is shown in FIG. 4. In this embodiment, the second jamming element 28 and the first jamming element 30 are positioned one after another on the piston rod 16. The coupling rod 42 extends between the locking jamming element 28 and the area of the actuator jamming element 30. In the rest position represented in FIG. 4, the coupling rod 42 is load-free so that the jamming element 28 locks on the piston rod 16. In contrast to the embodiment according to FIG. 1, the piston rod 16 can thus not be moved freely in the rest position. Furthermore, no movement of the piston rod 16 upon release of the actuating element 14 into the rest position takes place, which rest position is shown in FIG. 4. The actuating element 14, however, can be moved in the direction of arrow A further in the rearward direction past its rest position and reaches a release position. In this release position it acts via the support location 50 in the manner of a two-arm lever onto the coupling rod 42, and the coupling rod 42 acts onto the second jamming element 28 which is moved into a position in which the piston rod 16 is released.

A follower 46 for the actuator jamming element 30 is provided as a correspondingly enlarged projecting surface at the actuating element 14.

The actuating element 14 is pivotably supported at the housing 12 whereby axle stumps, not shown in the drawing and extending perpendicularly to the plane of the drawing, are supported in the housing 12. Instead of this arrangement, it is possible, according to another embodiment based on FIG. 4, to provide the actuating lever which is in the form of a two-arm lever embodied such that the two legs converge in the area of the free ends and extend laterally along the housing 12 toward the pivot axis 62. They penetrate the housing 12 from the exterior to the interior and form the support location 50 and the follower 46.

The entire travel stroke of the inventive adaptor 10 can be seen in FIG. 4 in the area of the cartridge sleeve 20. The cartridge sleeve 20 contains the non-represented highly viscous material, especially the dental filling material. In the rest position in which the piston rod 16 is in its rearward end position, a piston 64 is adjacent to the housing 12. The piston 64 is moved by any generated stroke resulting from the actuation of the actuating element 14 by a certain portion in the working direction (forward direction) until it is positioned adjacent to the outlet opening 66 of the cartridge 20. With each movement of the lever 14 a portion of dental filling material is dispensed form the outlet opening 66.

According to a modified embodiment it is suggested to allow a movement of the piston rod 16 only to the position at which the piston 64 is in its end position. For this purpose the step 68 shown in FIG. 1 is provided which, in the end position of the piston 641 reaches the area of the jamming element 30. Due to the reduced diameter of the piston rod 16 adjacent to the step 68, the jamming element 30 no longer engages the piston rod 16 so that further pressing of the lever 14 does not result in any forward movement of the piston rod 16.

Figure 5:
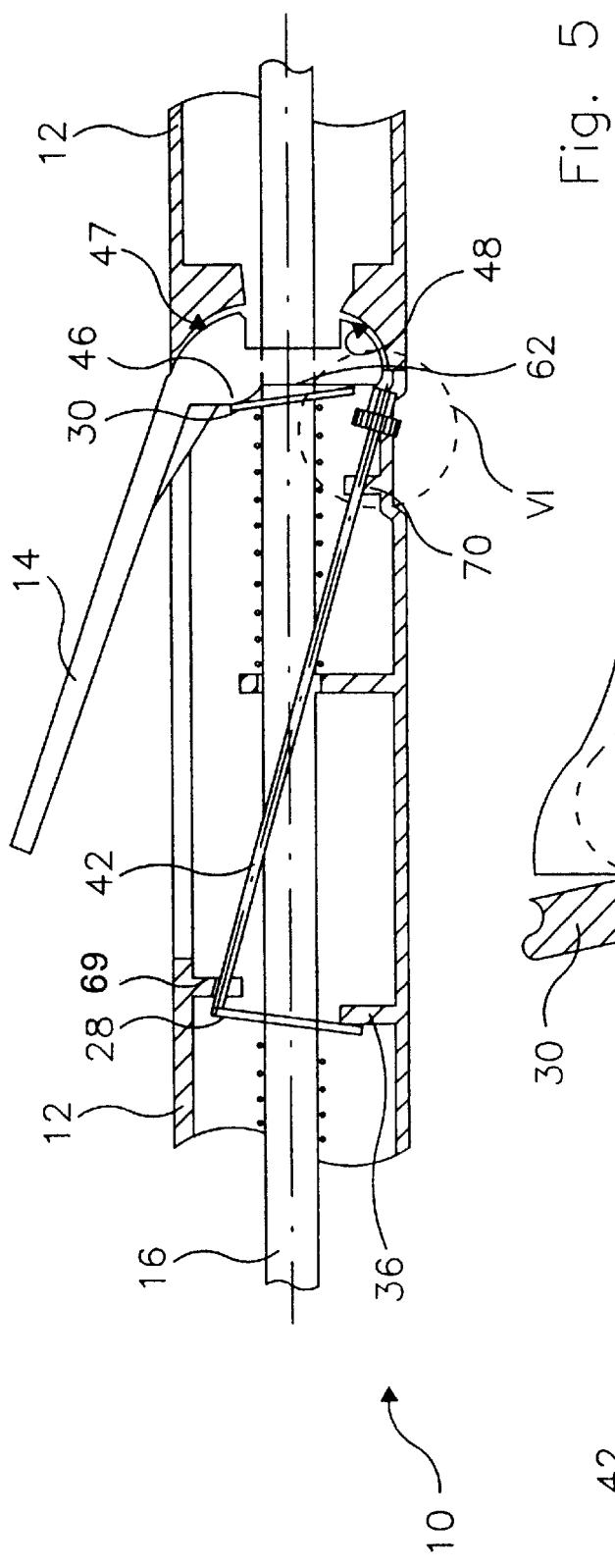
FIG. 5 is a sectional view of a part of a further embodiment of the inventive applicator.

A further embodiment of the inventive applicator is shown in FIG. 5. In this embodiment, the pivotable guiding of the actuating element 14 is realized by the guide surfaces 47 and 48 which are embodied at the pivotable actuating lever 14 and the housing 12. The guide surfaces 47 and 48 have a common radius so that the lever 14 can be pivoted about the pivot axle 62 without it being necessary that axle stumps penetrate the housing 12. Accordingly, the lever 14 extends in the area of the guide surfaces to both sides of the piston rods 16 and forms the follower 46 for the first jamming device 30 as well as the support location 50 for the coupling rod 42.

The coupling rod 42 is also glidingly supported at the housing 12 with a U-shaped receiving elements 69 and 70. In this embodiment, the coupling rod 42 extends at a slant to the piston rod 16.

In another embodiment it is suggested to switch the arrangement of the receiving element 69 for the coupling rod 42 and the bearing location 36 for the jamming element 28. The coupling rod 42 extends then substantially parallel to the piston rod 16. In this embodiment it is, however, necessary that the receiving elements 69 and 70 support the coupling rod in all directions, while in the shown embodiment according to FIG. 5 a support by the U-shaped receiving elements is sufficient.

Figure 6:
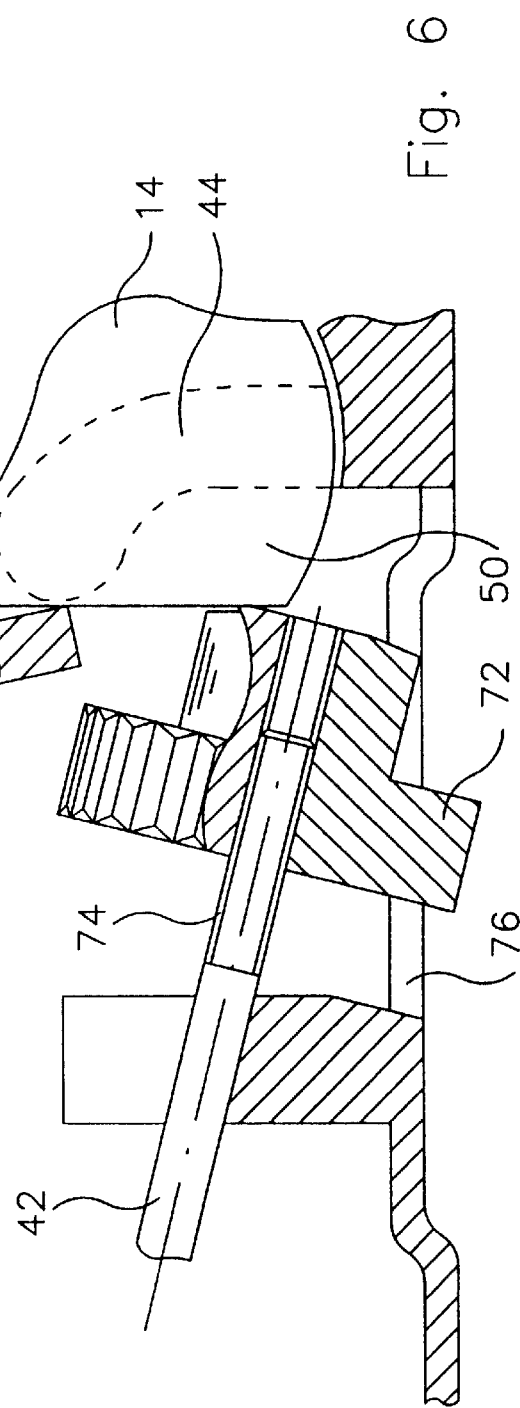
FIG. 6 is a detailed view of FIG. 5.

FIG. 6 shows a detail of the embodiment of FIG. 5 which represents the transition to the support of the coupling rod 42. As is shown in FIG. 6, the coupling rod 42 comprises a control device 72. With the control device 72, which is in the form of a knurled nut, it is possible to adjust either the effective distance between the jamming element 28 and the pressure surface or support location 50 or the tension of the coupling rod 42. The end of the coupling rod 42 comprises an exterior thread 74 and the knurled nut 72 a corresponding (matching) inner thread. The nut 72 can be actuated via an opening 76 of the housing. The nut 72 is preferably a self-securing nut and the area where it is located is covered with a non-represented cover so that only an adjustment for the applicator is provided.

With the nut 72 it is possible to adjust not only the stroke but also the tension of the coupling rod 42 in the rest position of the lever 14 (shown in FIG. 5) such that the jamming element 28 already releases the piston rod 16 in the rest position. Then, the piston rod 16 can be freely moved in the rest position so that the piston rod 16 can avoid applying pressure onto the paste material in the rest position. Upon a further rotation of the nut 72 in the direction of extending the coupling rod 42, the stroke of the piston rod 16 in the rearward direction, upon release of the actuating lever 14, can also be adjusted. In this embodiment of the inventive applicator, the forward movement of the piston rod 16 by complete actuation stroke of the actuating lever 14 is always identical, while the rearward movement and thus the stroke is adjustable.

In order to allow a movement of the piston rod 16 to the rear in the position of the control device 72 with the piston rod 16 being secured in the rest position for loading a new cartridge 20, the lever 14 can be pivoted into a release position in which it is pulled away from the housing 12. In this position the pressure surface 50 presses onto the control device 72 and thus onto the coupling rod 42 and simultaneously onto the jamming element 30 which is thus lifted off the support 44 connected to the housing. Both jamming elements 30 and 28 thus release the piston rod 16 so that it is freely displaceable.

Figure 7:
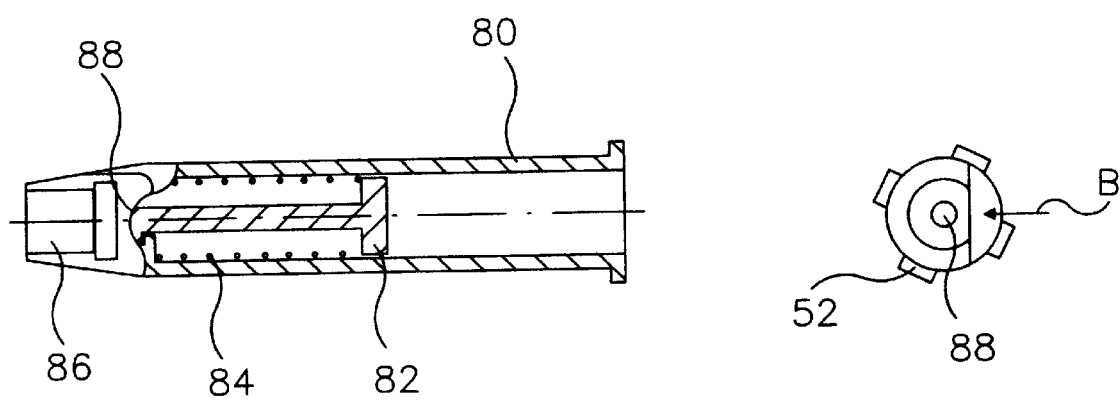
FIG. 7 is a part-sectional view of an adaptor for the inventive applicator.

According to a further embodiment, the attachment of a spring-loaded adaptor is provided, as can be seen in FIG. 7. The adaptor 80 is provided for engagement of the adaptor connector 22 of the housing and comprises a piston 82 which is spring loaded in the rearward direction of the non-represented piston rod. The piston rod 16 is designed to rest with its plunger 54 or its forward end at the piston 82. Due to the spring loading by the pressure spring 84, the piston rod 16, upon releasing the piston rod, for example, by moving the lever 14 into the release position, is returned into its initial position without requiring a manual return.

The adaptor 80 is designed such that a cartridge can be received in its cartridge receiving unit 86. For this purpose, the cartridge receiving unit is open at one end and a non-represented cartridge with dental filling material can be easily inserted into the adaptor 80 made of plastic by being pressed into it in the direction of arrow B. The piston 82 comprises at its forward end a projection 88 via which it is securely held at the adaptor 80.

According to a further especially advantageous embodiment it is suggested to provide the piston rod 16 in the engagement area of the actuator jamming element 30 with a micro toothing. Preferably, the micro toothing has a saw-tooth profile whereby the depth of the depressions is approximately 20 to 100 micrometer, preferably approximately 50 micrometer.

It is understood that the micro toothing can also be provided, if needed, in the area of the locking jamming element 28. Furthermore, for facilitating manufacture, it may be easier to provide the entire piston rod 16 with the micro toothing which does not affect the function of the inventive solution in any way.

The present invention is, of course, in no way restricted to the specific disclosure of the specification and drawings, but also encompasses any modifications within the scope of the appended claims.

What is claimed is:

1. An applicator for highly viscous materials, said applicator comprising:

a housing;

a first and a second jamming element positioned spaced from one another in a longitudinal direction in said housing;

a coupling rod connected to said second jamming element;

a piston rod supported in said housing;

an actuating element positioned in said housing and connected to said piston rod for moving said piston rod in a forward direction from an inactive position into an working position, whereby said actuating element is moved from a rest position into an operative position, and in a rearward direction from said working position into said inactive position;

wherein said first jamming element is jammed, when said actuating element actuates said piston rod in said forward direction, and is moved with said piston rod in said forward direction;

wherein said second jamming element is jammed by a spring force in said rearward direction so as to rest at said housing, when said actuating element actuates said piston rod in said forward direction; and wherein said actuating element, when moving said piston rod in said rearward direction, acts on said coupling rod for releasing said second jamming element.

2. An applicator according to claim 1, wherein said coupling rod in said rest position of said actuating element acts on said second jamming element and wherein said piston rod in said inactive position is freely moveable.

3. An applicator according to claim 1, wherein said actuating element is moveable past said rest position in said rearward direction into a release position such that said piston rod is freely moveable.

4. An applicator according to claim 1, wherein said actuating element is a handle extending in said rest position at an acute angle to said piston rod and is displaced toward said housing in order to reach said operative position and is moved away from said housing to return into said rest position.

5. An applicator according to claim 4, wherein said acute angle is approximately 26°.

6. An applicator according to claim 1, wherein, when said actuating element is moved from said rest position into said operative position, said first jamming element acts as a one-arm lever onto said piston rod and said actuating element is supported at said housing.

7. An applicator according to claim 6, wherein said actuating element is a lever spring-loaded into said rest position, said lever having a free end pointing substantially in said forward direction.

8. An applicator according to claim 1, wherein said actuating element comprises a follower acting onto said first jamming element such that, when said actuating element is moved from said rest position into said operative position, said first jamming element is pressed onto said piston rod in said forward direction.

9. An applicator according to claim 8, wherein said coupling rod extends between said second jamming element and said actuating element and is supported at a support location at said actuating element, wherein said support location is spaced from said follower.

10. An applicator according to claim 9, wherein said coupling rod extends at a slant to said piston rod and projects past said actuating element.

11. An applicator according to claim 8, wherein said coupling rod has opposite ends and a joint at each one of said opposite ends.

12. An applicator according to claim 8, wherein said coupling rod is a push rod and has a length such that upon return of said actuating element from said operative position into said rest position said second jamming element is released.

13. An applicator according to claim 1, wherein said second jamming element, viewed in said forward direction, is arranged in front of said actuating element.

14. An applicator according to claim 1, wherein said housing has an abutment for said first jamming element arranged such that in said rest position of said actuating element said second jamming element is positioned, without being jammed, on said piston rod.

15. An applicator according to claim 1, wherein said coupling rod is a release rod for ensuring jamming of said second jamming element during a last portion of a return travel of said actuating element into said rest position and said piston rod, during said return travel of said actuating element, is easily moveable in said rearward direction.

16. An applicator according to claim 1, comprising a connector for attaching thereto a cartridge containing a highly viscous material in the form of a dental filling material.

17. An applicator according to claim 1, wherein said piston rod has a rearward end projecting from said housing and having a marking for indicating an end position for a travel stroke of said piston rod in said forward direction corresponding to a complete emptying of a cartridge attached to a forward end of said housing, the cartridge containing a highly viscous material.

18. An applicator according to claim 1, wherein said housing comprises a connector for an adaptor, guiding a piston spring-loaded in said rearward direction and comprising a snap-on receiving member for a cartridge containing a light-curing dental filling material.

19. An applicator according to claim 1, wherein said coupling rod extends at an acute angle to said piston rod.

20. An applicator according to claim 1, wherein said piston rod has a step for disengaging, at the end of the travel stroke of said piston rod into said working position, said first jamming element from said piston rod.

21. An applicator according to claim 1, wherein said piston rod comprises a micro toothing at least in the area of said first jamming element.

* * * * *